(12) United States Patent
Chopra et al.

(10) Patent No.: US 11,793,992 B2
(45) Date of Patent: Oct. 24, 2023

(54) SYSTEMS AND METHODS FOR PUMP-ASSISTED BLOOD CIRCULATION

(71) Applicant: CARDIODYME, INC., New York, NY (US)

(72) Inventors: Gopal K. Chopra, New York, NY (US); William Graham, Houston, TX (US)

(73) Assignee: CARDIODYME, INC., New York, NY (US)

( * ) Notice: Subject to any disclaimer, the term of this patent is extended or adjusted under 35 U.S.C. 154(b) by 0 days.

(21) Appl. No.: 18/183,640

(22) Filed: Mar. 14, 2023

(65) Prior Publication Data
US 2023/0211144 A1 Jul. 6, 2023

Related U.S. Application Data

(63) Continuation of application No. PCT/US2022/076474, filed on Sep. 15, 2022.

(60) Provisional application No. 63/245,039, filed on Sep. 16, 2021.

(51) Int. Cl.
| | |
|---|---|
| *A61M 60/857* | (2021.01) |
| *A61M 60/174* | (2021.01) |
| *A61M 60/148* | (2021.01) |
| *A61M 60/403* | (2021.01) |
| *A61M 60/806* | (2021.01) |

(52) U.S. Cl.
CPC ........ *A61M 60/148* (2021.01); *A61M 60/403* (2021.01); *A61M 60/806* (2021.01)

(58) Field of Classification Search
CPC .............. A61M 60/148; A61M 60/178; A61M 60/237; A61M 60/422; A61M 2205/04; A61M 2205/103; A61M 2210/125; A61M 60/174; A61M 60/419; A61M 60/538; A61M 60/806; A61M 60/824; A61M 60/825; A61M 60/857; A61M 60/861; A61M 60/863; Y10S 415/90
See application file for complete search history.

(56) References Cited

U.S. PATENT DOCUMENTS

| | | | |
|---|---|---|---|
| 5,947,892 | A | 9/1999 | Benkowski et al. |
| 6,135,729 | A | 10/2000 | Aber |
| 2005/0135948 | A1 | 6/2005 | Olsen et al. |
| 2009/0203957 | A1 | 8/2009 | Larose et al. |
| 2016/0038663 | A1 | 2/2016 | Taskin |

*Primary Examiner* — Jon Eric C Morales
(74) *Attorney, Agent, or Firm* — Bookoff McAndrews, PLLC (57) ABSTRACT

A system for assisting a circulation of blood inside a body of a patient includes a pump including: a housing having an upstream portion and a downstream portion; an inducer positioned in the upstream portion of the housing, the inducer including one or more helically-wound inducer blades to rotate around a longitudinal axis of the pump; an impeller positioned downstream of the inducer in the housing, the impeller including one or more impeller blades to rotate around the longitudinal axis of the pump; and a diffuser positioned in the downstream portion of the housing, to direct blood through at least one aperture in a circumference of the housing.

20 Claims, 5 Drawing Sheets

SYSTEMS AND METHODS FOR PUMP-ASSISTED BLOOD CIRCULATION

CROSS-REFERENCE TO RELATED APPLICATION(S)

This application is a continuation application under 35 U.S.C. § 111(a) of pending International Application No. PCT/US2022/076474, filed Sep. 15, 2022, which claims the benefit of priority to U.S. Application No. 63/245,039, filed Sep. 16, 2021, the entireties of which are incorporated herein by reference.

TECHNICAL FIELD

Various aspects of the disclosure relate generally to systems and methods for using a pump to assist in blood circulation. According to examples, the disclosure relates to systems, devices, and related methods for use and control of an axial flow pump to provide circulatory assistance or bypass. In embodiments, the pump may be a multi-stage axial flow pump used to circulate blood in intravascular applications.

BACKGROUND

In a patient with a heart condition, lung condition or intra and post procedure on the heart, the heart may have difficulty circulating blood through the patient's body. For example, a patient with heart failure can have insufficient ventricular blood output due to issues with the strength or rhythm of the contraction of one or more chambers of the heart. In other situations, such as surgical or ambulatory settings, it may be necessary to bypass some or all blood flow. In such cases, pumps may be implanted in the heart or other portions of the vascular system (e.g. an artery) or otherwise connected to the patient's circulatory system to assist or bypass the heart. The pumps may improve blood flow in general in the body or substantially improve flow to a specific region, such as the renal arteries to the kidneys, for which the pump must have local and directional control of the flow.

The present disclosure is directed to methods and systems focused on addressing one or more of these above-referenced challenges or other challenges in the art.

SUMMARY

In some aspects, the techniques described herein relate to a system for assisting a circulation of blood inside a body of a patient, the system including: a pump including: a housing having an upstream portion and a downstream portion; an inducer positioned in the upstream portion of the housing, the inducer including one or more helically-wound inducer blades to rotate around a longitudinal axis of the pump; an impeller positioned downstream of the inducer in the housing, the impeller including one or more impeller blades to rotate around the longitudinal axis of the pump; and a diffuser positioned in the downstream portion of the housing, to direct blood through at least one aperture in a circumference of the housing.

In some aspects, the techniques described herein relate to a system, wherein the inducer and the impeller are rotatable relative to the housing and the diffuser.

In some aspects, the techniques described herein relate to a system, further including: a catheter with an upstream portion and a downstream portion, wherein the upstream portion of the catheter includes a blood flow inlet to deliver blood through the catheter from the blood flow inlet to the helical inducer.

In some aspects, the techniques described herein relate to a system, further including: a pump cable connected to the pump to provide an electrical pathway between the pump and one or more of a sensor or controller outside the body of the patient.

In some aspects, the techniques described herein relate to a system, wherein the at least one aperture includes at least two apertures defined by cylindrical portions of the housing at distal and proximal portions of the at least two apertures and strut-like portions of the housing at radial sides of the at least two apertures.

In some aspects, the techniques described herein relate to a system, wherein the one or more helically-wound inducer blades rotate to initially accelerate blood in the housing, the one or more impeller blades rotate to increase a rotational velocity of the blood imparted by the inducer, and the diffuser includes two or more curved fins to convert the rotational velocity of the blood imparted by the impeller into an axial velocity through the at least one aperture.

In some aspects, the techniques described herein relate to a system, wherein the one or more helically-wound inducer blades have a pitch that varies along an axial length of the inducer.

In some aspects, the techniques described herein relate to a system, wherein the one or more impeller blades are approximately aligned with the longitudinal axis of the pump.

In some aspects, the techniques described herein relate to a system, wherein the one or more impeller blades have an arc shape in an upstream portion of the impeller and a relatively straight shape in a downstream portion of the impeller.

In some aspects, the techniques described herein relate to a system, wherein the pump further includes a shaft, and wherein the diffuser is stationary in the housing, and the diffuser further includes a bearing mount to support the shaft while allowing the shaft to rotate in the diffuser.

In some aspects, the techniques described herein relate to a system, wherein the inducer and the impeller are mounted on the shaft to rotate in the housing.

In some aspects, the techniques described herein relate to a system, wherein the pump further includes a motor secured to one or more of the downstream portion of the housing or a downstream portion of the diffuser, and operatively connected to the shaft to rotate the shaft and thereby rotate the inducer and the impeller relative to the housing and the diffuser.

In some aspects, the techniques described herein relate to a system, wherein one or more of the inducer and the impeller include hermetically sealed magnets, and wherein the pump further includes a stator to rotate the hermetically sealed magnets around the shaft to thereby rotate the inducer and the impeller relative to the housing and the diffuser.

In some aspects, the techniques described herein relate to a system, wherein the stator has a C-shape encompassing less than a 360 degree circumference of the housing.

In some aspects, the techniques described herein relate to a system, wherein one or more of the inducer and the impeller include hermetically sealed magnets, and wherein the system further includes an external stator contained in a flexible pad or strap configured to be adhered to or wrapped around the body of the patient, the external stator to rotate the hermetically sealed magnets around the shaft to thereby rotate the inducer and the impeller relative to the housing and the diffuser.

Aspects of the disclosure relate to, among other things, systems, devices, and methods that employ a pump to assist or support blood flow. In embodiments, an axial-flow pump aids blood circulation. Each of the aspects disclosed herein may include one or more of the features described in connection with any of the other disclosed aspects.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated herein and constitute a part of this specification, illustrate exemplary aspects of the disclosure and, together with the description, explain the principles of the disclosure.

DETAILED DESCRIPTION

Aspects of this disclosure relate to systems and methods for using a multi-stage axial flow pump to circulate blood in intracorporeal applications. An axial flow pump in accordance with the present disclosure may be positioned in a heart chamber, an artery, or a vein, via a catheter. In such intracorporeal applications, the pump may be a component in a system that aids the heart in circulating blood.

Intravascular blood pumps are circulatory assist devices that may be implanted into the vascular system or heart of a patient percutaneously and/or surgically. These devices may assist circulation by increasing the volume of blood being ejected from the left or right side of the heart. Intravascular pumps, such as axial flow blood pumps, can be coupled to the distal end of a flexible catheter, and the catheter may be inserted into the vascular system.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user and thus further along the vasculature in the patient. Similarly, extends "distally" indicates that a component extends in a distal direction, and extends "proximally" indicates that a component extends in a proximal direction. Portions of the disclosed devices and/or their components are also referred to as upstream and downstream portions, with the term "upstream" intended to refer to portions closer to the source of the blood flow, and the term "downstream" used herein to refer to portions further away from the source of the blood flow. Further, as used herein, the terms "about," "approximately," and "substantially" indicate a range of values within +/−10% of a stated or implied value. Additionally, terms that indicate the geometric shape of a component/surface refer to exact and approximate shapes.

According to an embodiment of this disclosure, a pump is used to assist in delivering blood to another site in the circulatory system. Although this disclosure describes an embodiment wherein the pump is positioned in the ascending aorta, the disclosure is not limited to such use. Aspects of the disclosure may also be used for delivering blood from a heart chamber (i.e., left ventricle, right ventricle, right atrium, or left atrium), artery, or vein, to another portion of the circulatory system (e.g. an artery, a vein, or other heart chamber), or from an upstream portion of an artery or a vein to a downstream portion of that same artery or vein. A circulatory assist device in accordance with this disclosure may be a rotary axial-flow mechanical ventricular assist pump, and may be positioned in, for example, the left ventricle (LV) in order to assist the heart in pumping blood into the ascending aorta.

Figure 1:
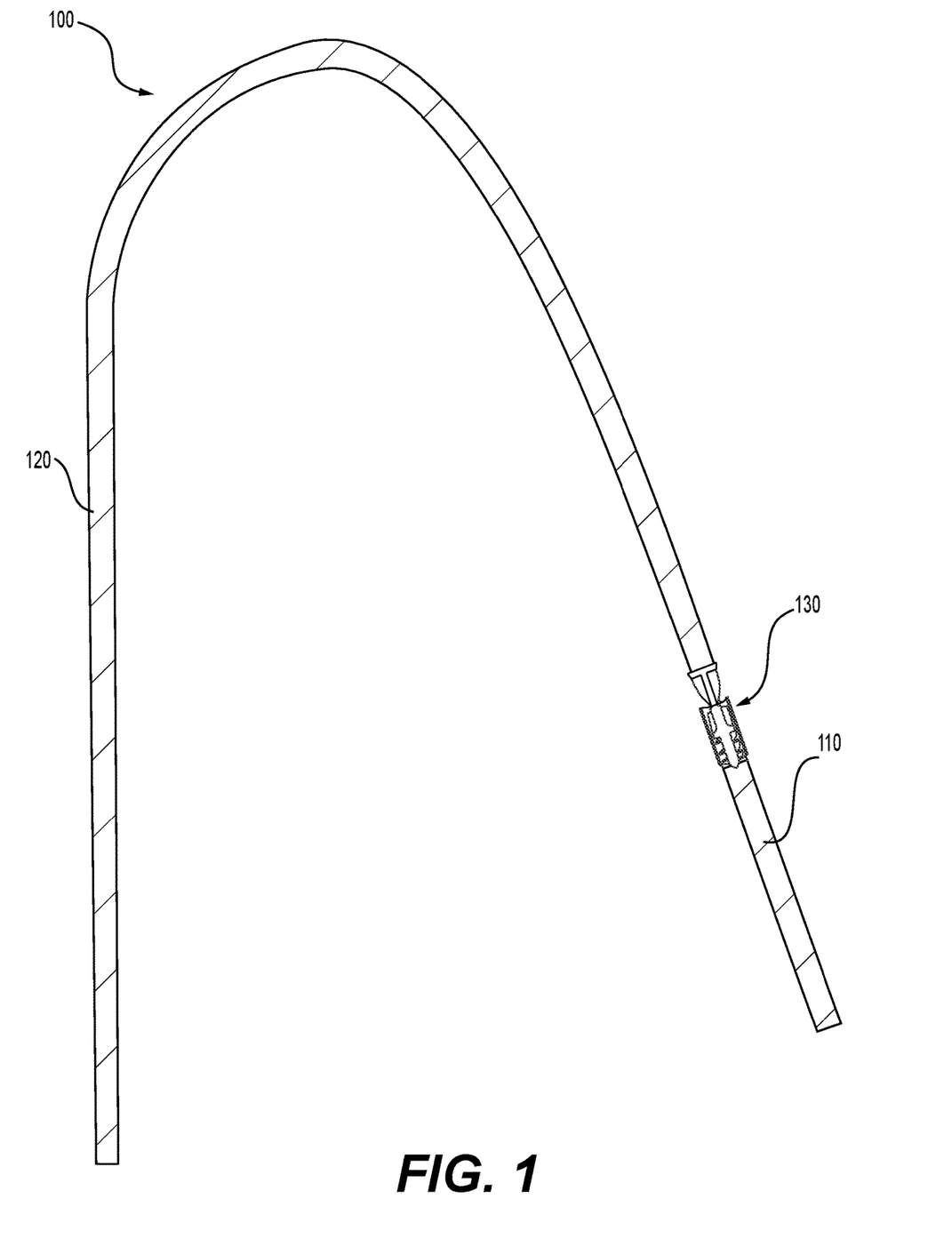
FIG. 1 is an illustration of a catheter pump assembly, according to aspects of this disclosure.
Figure 2:
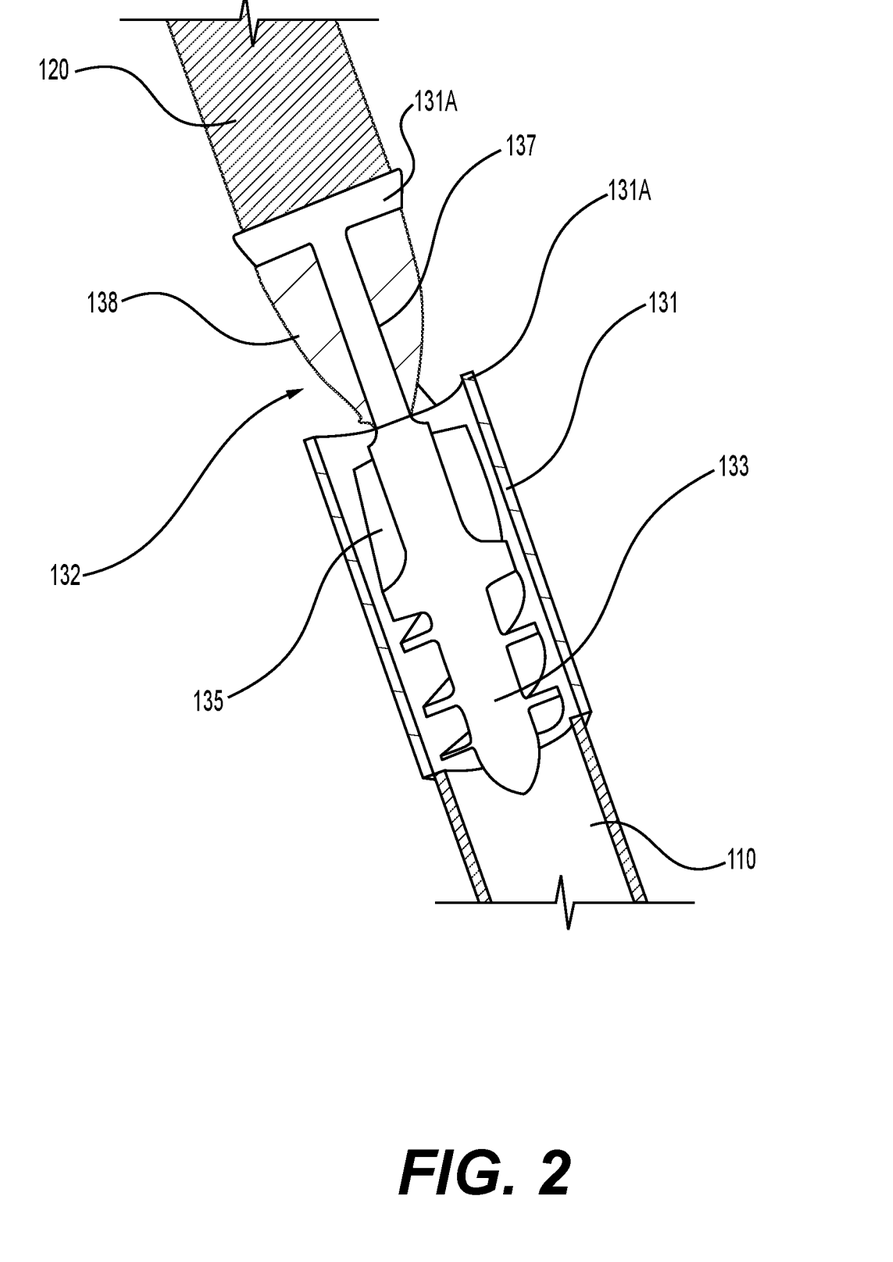
FIG. 2 is a cross-sectional illustration of the pump portion of the catheter pump assembly of FIG. 1, according to aspects of this disclosure.
Figure 3:
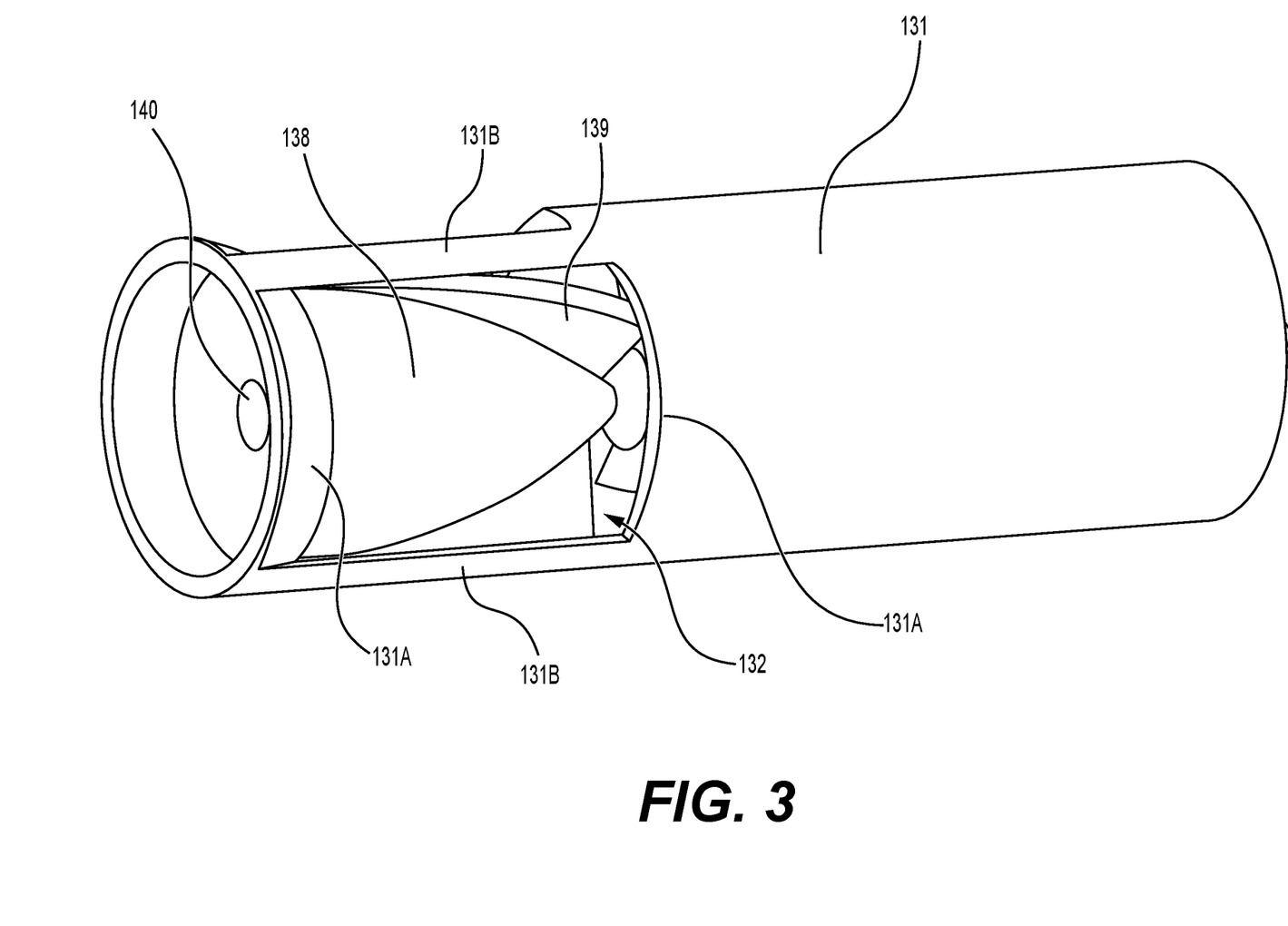
FIG. 3 is a perspective view of a pump assembly, according to aspects of this disclosure.
Figure 4:
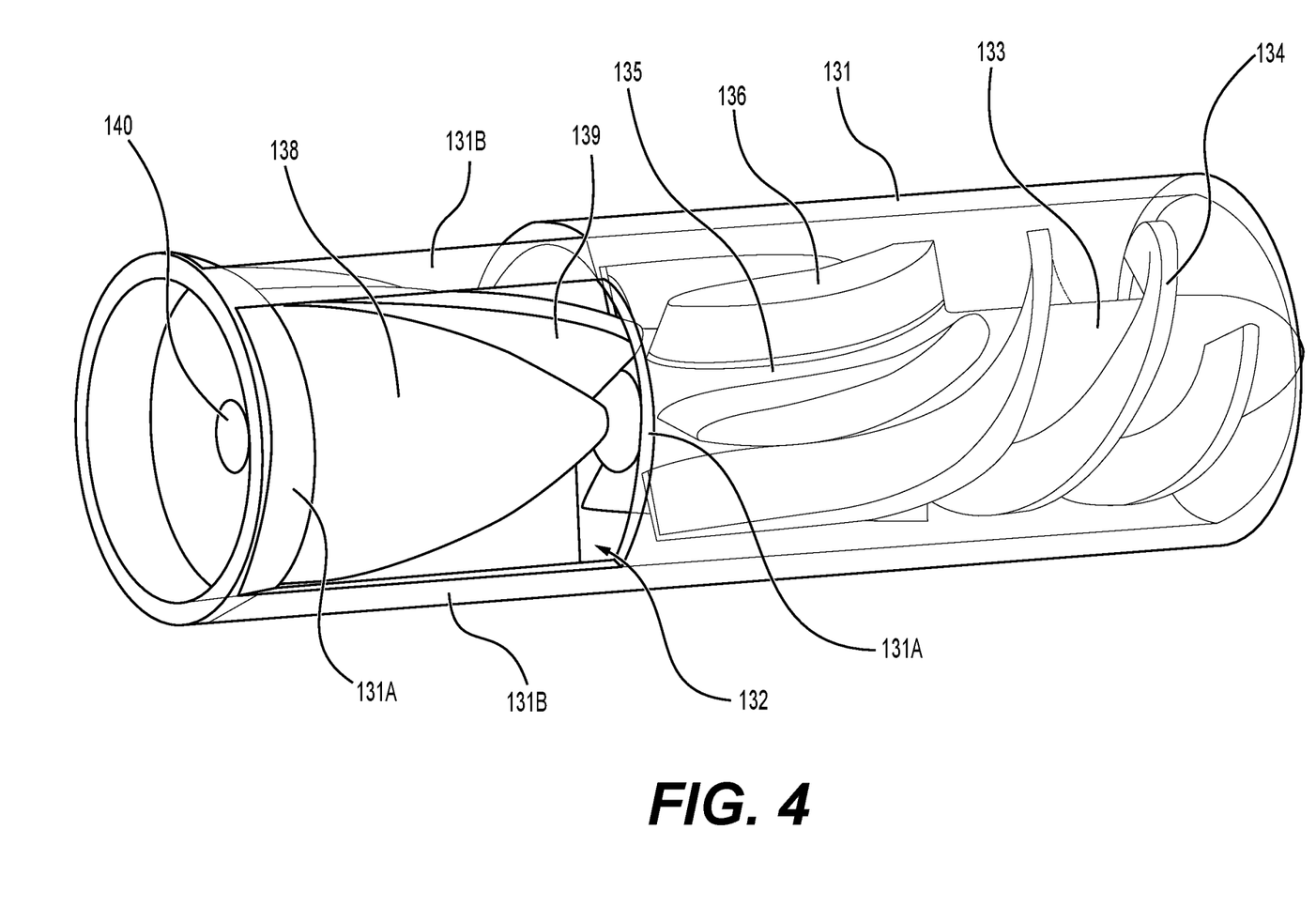
FIG. 4 is a perspective view of the pump assembly of FIG. 3, with the housing shown as transparent for viewing the internal components, according to aspects of this disclosure.

A catheter pump assembly 100 in accordance with the present disclosure is shown in FIG. 1, and the catheter pump portion of the assembly is shown in FIG. 2. A portion of a catheter pump assembly, including the inducer, impeller, and diffuser portions, is shown in FIG. 3, and that portion is also shown in FIG. 4 with the housing rendered partially transparent.

With reference to FIG. 1, one embodiment of a catheter pump assembly 100 is shown. The assembly 100 generally includes a catheter 110 with a blood flow inlet, a pump cable 120, and a pump 130. The assembly 100 is configured to be inserted into a blood vessel, such as an artery, and to assist in pumping blood, for example, from within a chamber of the heart to an artery.

Catheter 110 and pump 130 may be inserted into the artery in a variety of ways, and properly positioning the pump within the artery can be a challenge due to the shape and size of the blood vessels. In one embodiment, this challenge may be addressed by the use of railroad-like guidewires. After inserting the guidewire into the artery, catheter 110 can follow the guidewire until it reaches the desired position. The guidewire may then be removed, leaving catheter 110 and pump 130 in place, with pump cable 120 extending from pump 130, through catheter 110, and to the outside of the body of the patient. Pump cable 120 may supply power to pump 130, send or receive signals from one or more sensors or controllers, and/or serve another purpose requiring an electrical pathway from the organ or vessel to the outside of the body to, for example, a controller and/or power source.

Catheter 110 can be, for example, a 30 Fr catheter having a 10 mm outer diameter and one or more lumens extending therethrough. Other sizes may be suitable for the particular application. Catheter 110 may be comprised of a flexible biocompatible material, such as medical grade plastics. The portion of catheter 110 downstream of pump 130 includes a lumen that accommodates pump cable 120. The portion of catheter 110 upstream of pump 130 includes a lumen for blood flow from a distal opening of catheter 110 to pump 130. In some embodiments, the portion of catheter 110 upstream of pump 130 may be perforated to provide for alternate entry of blood into pump 130. Catheter 110 may include a stent (not shown) for anchoring catheter 110 in place within a blood vessel or heart chamber. The stent may be a collapsible/expandable structure known to those of skill in the art, and may be deployed by any conventional methods. Other structures for anchoring catheter 110, and thereby inhibiting migration of pump 130, may be used, such as an anchoring balloon at a distal end of catheter 110.

The pump 130 can include a housing 131 for encasing the internal components of pump 130. In some embodiments, housing 131 may have an outer diameter of 7-8 mm and be machined from sintered titanium or other suitably biocompatible material, although other sizes and materials may be used. Housing 131 can contain a helical inducer 133 (a first stage of pump 130), an impeller 135 (a second stage of pump 130), and a blood diffuser 138 (a third stage of pump 130). A distal, or upstream, portion of housing 131 may serve to encase helical inducer 133 and impeller 135 completely. A proximal, or downstream, portion of housing 131 may partially cover blood diffuser 138, while also including one or more exit apertures 132 that permit the pumped blood flow to exit pump 130. In some embodiments, exit apertures 132 may be defined by cylindrical portions 131A of housing 131 at the distal and proximal portions of exit apertures 132, and strut-like portions 131B of housing 131 at the radial sides of exit apertures 132. FIGS. 3 and 4 show three strut-like portions 131B circumferentially spaced approximately equally, 120 degrees apart. Strut-like portions 131B extend between cylindrical portions 131A, may be integrally-molded with cylindrical portions 131A, and define three exit apertures 132. More or less strut-like portions 131B, and resulting exit apertures 132, as well as unequal spacing between strut-like portions 131B, may be used.

In some embodiments, exit apertures 132 may be configured to direct flow to a particular vessel with the appropriate radiologic marking in order to aid in proper positioning and fixation. The pump 130 may have three stages and may spread acceleration of blood over a relatively large length (approximately 1-2 inches) and over a sufficient amount of time, resulting in a low shear and less harm to blood cells, and inhibiting the accumulation and formation of thrombus. An embodiment of pump 130 connected to catheter 110 and pump cable 120 is illustrated in FIG. 2.

The helical inducer 133 may have one or more helically-wound inducer blades 134. The helical inducer 133 of pump 130 provides the initial acceleration of blood. The length of helical inducer 133 can be varied to change flow rates and pressure. In addition, the pitch of inducer blades 134 can affect hemolysis and shear such that a steeper pitch can enable faster flow and a reduction in hemolysis, which may be beneficial in lower pressure applications. The helix angle of inducer blades 134 can be reduced to increase the blood intake per revolution and lower pressure capability, or increased to decrease the blood intake per revolution and increase pressure capability. In some embodiments, the helically wound inducer blades 134 have a pitch that varies along the axial length of helical inducer 133 and impeller 135 such that the pitch of helically wound inducer blades 134 in the helical inducer 133 is less than the pitch of helically wound inducer blades 134 in impeller 135. An exemplary length of helical inducer 133 is approximately 5 mm to approximately 2 cm. An exemplary pitch is approximately 22 degrees.

In some embodiments, the impeller 135 can include multiple straight or approximately straight impeller blades 136 (i.e., the blades are aligned or approximately aligned with a longitudinal axis of pump 130). Impeller blades 136 may be interspersed between helically wound inducer blades 134 (e.g. alternate circumferentially with inducer blades 134), and have an initial arc shape that flattens out (becoming essentially linear) as impeller blades 136 approach the downstream end of impeller 135. Both helically wound inducer blades 134 and impeller blades 136 may run substantially parallel to one another and be equally spaced about impeller 135 at the downstream end thereof. Impeller 135 may be connected to a shaft 137 to provide the impeller 135 and helical inducer 133 with an axis about which to rotate. The impeller blade thickness and angle may be adjusted to pair with a diffuser appropriate for the desired pressure and flow characteristics of the design.

In order to improve the efficiency of pump 130, the particular dimensions and contours of helically wound inducer blades 134 and impeller blades 136 may be adjusted based on the flow rate and pressure requirements for a given clinical application.

As illustrated in FIGS. 3 and 4, the blood diffuser 138 (stage three of pump 130) can be positioned at the downstream end of the impeller 135, and can be configured to convert the rotational velocity of the blood imparted by impeller 135 into axial velocity and blood pump outflow by de-spinning the blood flow. The use of two or more curved fins 139 may slow the rotational velocity of the blood flow, while the contour of the body of blood diffuser 138 may direct the blood flow out through one or more exit apertures 132 in housing 131. The number, thickness, angle, and proximity of the curved fins 139 to the impeller 135 may be adjusted to achieve desired pressure and flow characteristics. No blood flows in the area just proximal of blood diffuser 138 on an end of pump 130 nearest to pump cable 120.

Figure 5:
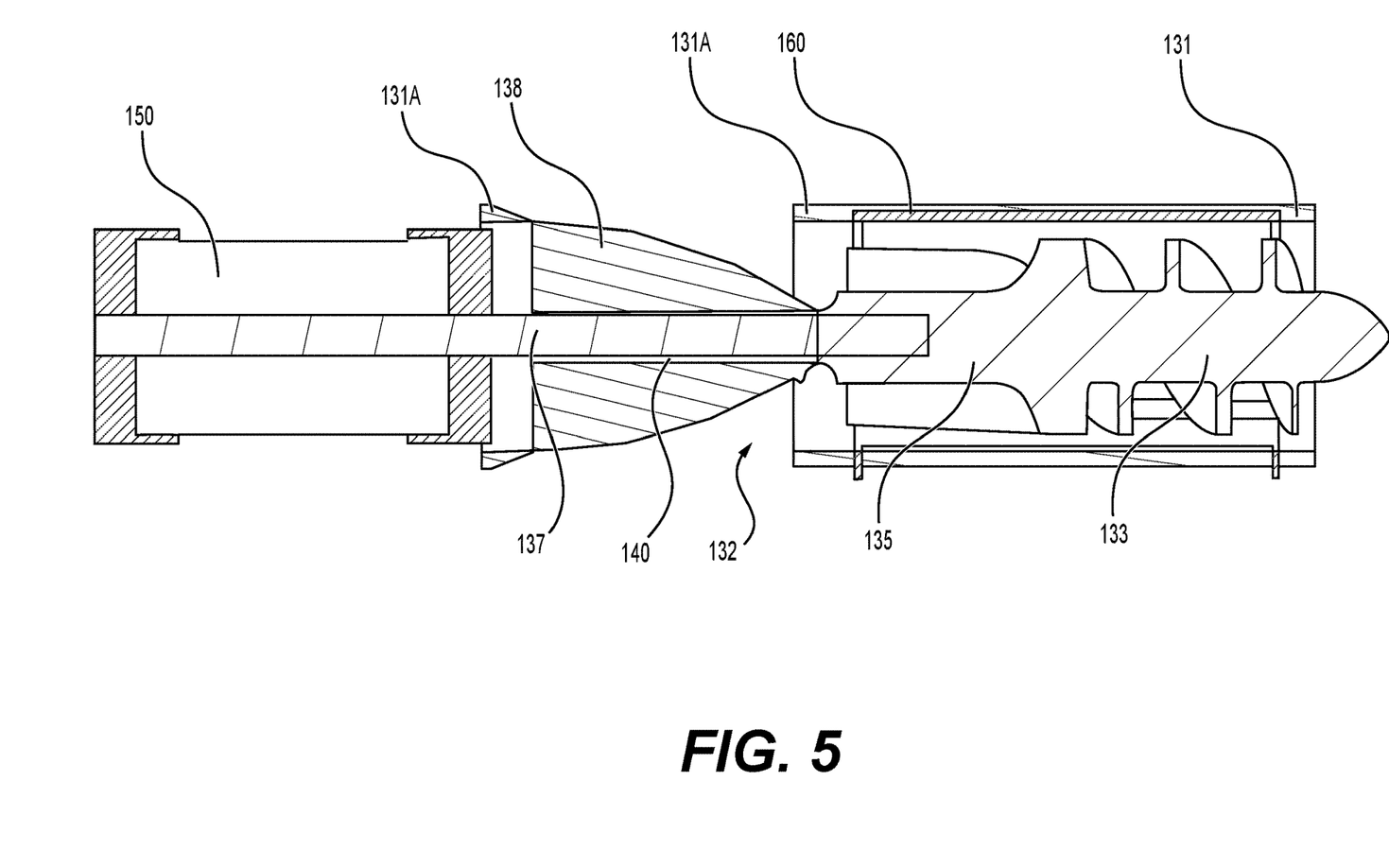
FIG. 5 is a cross-sectional view of a pump assembly, according to aspects of this disclosure.

In some embodiments, as illustrated in FIG. 5, blood diffuser 138 may also serve as the bearing mount for shaft 137. An internal surface of blood diffuser 138 may be a bearing surface 140, and may be configured to support shaft 137 while allowing shaft 137 to rotate. The length of the bearing surface 140 may allow impeller 135 and helical inducer 133 to be fully supported by the blood diffuser 138, thus eliminating the need for a separate bearing on the distal end of impeller 135 and helical inducer 133. In some embodiments, blood diffuser 138 may be a stationary component, as reducing the number of moving parts can aid in reliability, manufacturability, and system efficiency. In some embodiments, shaft 137, impeller 135, and helical inducer 133 may be the only moving pump components, where helical inducer 133 and impeller 135 are rotatable relative to housing 131 and blood diffuser 138. These components may rotate at approximately 8,000 to approximately 14,000 RPM.

In some embodiments, impeller 135 and helical inducer 133 may be driven by a motor 150 positioned on the proximal portion of blood diffuser 138 opposite the impeller 135. The motor 150 may be secured to the proximal portion of housing 131 and/or blood diffuser 138, and may be operatively connected to shaft 137. As motor 150 rotates, motor 150 can rotate shaft 137, and shaft 137 (being connected to impeller 135 at a distal end thereof) may in turn rotate impeller 135 and helical inducer 133. The motor 150 may be powered by wires running through pump cable 120 to the outside of the patient, or by another suitable source. Motor 150 may be selected to be sized appropriately for a diameter of housing 131 and catheter 110, while still having sufficient power to provide the desired blood flow rates.

In some embodiments, in lieu of or in addition to motor 150, impeller 135 and/or helical inducer 133 may be formed with hermetically sealed magnets such that a stator 160 can drive impeller 135 and helical inducer 133 directly. These magnets can allow impeller 135 and helical inducer 133 to be driven by, for example, a brushless, direct current (DC) stator 160. In some embodiments, the stator 160 may be formed in the portion of housing 131 surrounding impeller 135 and/or helical inducer 133, and be powered and controlled via wiring that passes through pump cable 120 to the outside of the patient. In some embodiments, stator 160 may be a partial stator in a C-shape, where the partial stator does not encompass a 360 degree circumference.

In some embodiments, impeller 135 and helical inducer 133 may be driven transcutaneously via an external stator (not shown). An external stator may be, for example, contained in a flexible pad or strap configured to be adhered to and/or wrapped around the body of a patient in a region adjacent to the pump 130, such as around the torso of the patient. Embodiments of a flexible pad may be, for example, approximately 40 inches long and 5 inches wide, and may be positioned to be close to the position of pump 130 or up to approximately 12 inches away from the pump 130. In some embodiments, the flexible pad may be formed in a C-shape, and provide a stator covering a 180-degree arc around pump 130. Here, the external stator may be a partial stator in a C-shape, where the partial stator does not encompass a 360 degree circumference. Such an external stator may cause impeller 135 and helical inducer 133 to rotate by generating a dynamic magnetic field. In these transcutaneous applications, the pump assembly may be able to be shorter in overall length as compared to micro-motor powered applications, due to the lack of a need for drive components on the side of the blood diffuser 138 opposite the impeller 135. Further, as compared to applications having the stator 160 incorporated into housing 131, transcutaneous stator applications may be able to have a smaller overall diameter, as housing 131 would not need to incorporate the drive elements of stator 160.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only, with a true scope of the disclosure being indicated by the following claims and their equivalents.

What is claimed is:

1. A system for assisting a circulation of blood inside a body of a patient, the system comprising:
    a pump including:
    a housing having an upstream portion and a downstream portion;
    an inducer positioned in the upstream portion of the housing, the inducer including one or more helically-wound inducer blades to rotate around a longitudinal axis of the pump;
    an impeller positioned downstream of the inducer in the housing, the impeller including one or more impeller blades to rotate around the longitudinal axis of the pump;
    a diffuser positioned in the downstream portion of the housing, to direct blood through at least one aperture in a circumference of the housing; and
    a stator to rotate the inducer and the impeller relative to the housing and the diffuser, wherein the stator has a C-shape encompassing less than a 360 degree circumference of the housing.

2. The system of claim 1, wherein the one or more helically-wound inducer blades are approximately parallel to the one or more impeller blades.

3. The system of claim 1, further comprising:
    a catheter with an upstream portion and a downstream portion, wherein the upstream portion of the catheter includes a blood flow inlet to deliver blood through the catheter from the blood flow inlet to the inducer.

4. The system of claim 1, further comprising:
    a pump cable connected to the pump to provide an electrical pathway between the pump and one or more of a sensor or controller outside the body of the patient.

5. The system of claim 1, wherein the at least one aperture includes at least two apertures defined by cylindrical portions of the housing at distal and proximal portions of the at least two apertures and strut-like portions of the housing at radial sides of the at least two apertures.

6. The system of claim 1, wherein
    the one or more helically-wound inducer blades rotate to initially accelerate blood in the housing,
    the one or more impeller blades rotate to increase a rotational velocity of the blood imparted by the inducer, and
    the diffuser includes two or more curved fins to convert the rotational velocity of the blood imparted by the impeller into an axial velocity through the at least one aperture.

7. The system of claim 1, wherein the one or more helically-wound inducer blades have a pitch that varies along an axial length of the inducer.

8. The system of claim 1, wherein the one or more impeller blades are approximately aligned with the longitudinal axis of the pump.

9. The system of claim 1, wherein the one or more impeller blades have an arc shape in an upstream portion of the impeller and a relatively straight shape in a downstream portion of the impeller.

10. The system of claim 1, wherein the pump further includes a shaft, and
    wherein the diffuser is stationary in the housing, and the diffuser further includes a bearing mount to support the shaft while allowing the shaft to rotate in the diffuser.

11. The system of claim 10, wherein the inducer and the impeller are mounted on the shaft to rotate in the housing.

12. The system of claim 11, wherein the pump further includes a motor secured to one or more of the downstream portion of the housing or a downstream portion of the diffuser, and operatively connected to the shaft to rotate the shaft and thereby rotate the inducer and the impeller relative to the housing and the diffuser.

13. The system of claim 11, wherein one or more of the inducer and the impeller include hermetically sealed magnets, and
    wherein the stator is configured to rotate the hermetically sealed magnets around the shaft to thereby rotate the inducer and the impeller relative to the housing and the diffuser.

14. The system of claim 1, wherein the stator includes an external stator configured to be adhered to or wrapped around the body of the patient.

15. A system for assisting a circulation of blood inside a body of a patient, the system comprising:
    a pump including:
    a housing having an upstream portion and a downstream portion;
    an inducer positioned in the upstream portion of the housing, the inducer including one or more helically-wound inducer blades to rotate around a longitudinal axis of the pump;
    an impeller positioned downstream of the inducer in the housing, the impeller including one or more impeller blades to rotate around the longitudinal axis of the pump;

a diffuser positioned in the downstream portion of the housing, to direct blood through at least one aperture in a circumference of the housing; and an external stator configured to be adhered to or wrapped around the body of the patient, the external stator configured to rotate the inducer and the impeller relative to the housing and the diffuser.

16. The system of claim 15, wherein the external stator has a C-shape encompassing less than a 360 degree circumference of the housing.

17. The system of claim 15, wherein the external stator is contained in a flexible pad or strap configured to be adhered to or wrapped around the body of the patient.

18. The system of claim 15, wherein:

the pump further includes a shaft, the inducer and the impeller are mounted on the shaft to rotate in the housing, one or more of the inducer and the impeller include hermetically sealed magnets, and the external stator is configured to rotate the hermetically sealed magnets around the shaft to thereby rotate the inducer and the impeller relative to the housing and the diffuser.

19. The system of claim 15, further comprising:

a catheter with an upstream portion and a downstream portion, wherein the upstream portion of the catheter includes a blood flow inlet to deliver blood through the catheter from the blood flow inlet to the inducer, and a pump cable connected to the pump to provide an electrical pathway between the pump and one or more of a sensor or controller outside the body of the patient.

20. The system of claim 15, wherein the at least one aperture includes at least two apertures defined by cylindrical portions of the housing at distal and proximal portions of the at least two apertures and strut-like portions of the housing at radial sides of the at least two apertures.

* * * * *